United States Patent [19]

Buchholz et al.

[11] Patent Number: 4,746,615
[45] Date of Patent: May 24, 1988

[54] STERILIZABLE FLUIDIZED BED FERMENTER

[75] Inventors: Rainer Buchholz, Unnau-Korb; Hans-Matthias Deger, Hofheim am Taunus; Hartmut Voelskow, Hattersheim; Rolf Woernle, Bad Soden am Taunus, all of Fed. Rep. of Germany

[73] Assignee: Hoechst Aktiengesellschaft, Fed. Rep. of Germany

[21] Appl. No.: 78,681

[22] Filed: Jul. 28, 1987

[30] Foreign Application Priority Data

Jul. 30, 1986 [DE] Fed. Rep. of Germany ....... 3625698

[51] Int. Cl.$^4$ .............................................. C12M 1/12
[52] U.S. Cl. .................... 435/311; 435/289; 435/313; 435/314; 435/813
[58] Field of Search ............... 435/289, 311, 313, 314, 435/813

[56] References Cited

U.S. PATENT DOCUMENTS

| | | |
|---|---|---|
| 4,046,921 | 9/1977 | Akao et al. ........................... 426/46 |
| 4,276,384 | 6/1981 | Mueller ................................ 435/311 |
| 4,282,328 | 8/1981 | Fukuda et al. ...................... 435/255 |
| 4,337,315 | 6/1982 | Fukushima et al. ................ 435/313 |
| 4,348,476 | 9/1982 | Hou ..................................... 435/123 |
| 4,447,534 | 5/1984 | Moebus et al. ...................... 435/161 |
| 4,686,189 | 8/1987 | Redikultsev et al. ............... 435/289 |

FOREIGN PATENT DOCUMENTS

| | | |
|---|---|---|
| 0058426 | 2/1982 | European Pat. Off. . |
| 0106146 | 9/1983 | European Pat. Off. . |
| 59-95879 | 6/1984 | Japan .................................. 435/311 |
| 13819 | of 1905 | United Kingdom ................ 435/313 |

*Primary Examiner*—Samuel Scott
*Assistant Examiner*—Allen J. Flanigan
*Attorney, Agent, or Firm*—Finnegan, Henderson, Farabow, Garrett & Dunner

[57] ABSTRACT

It is possible by use of a sterilizable fluidized bed fermenter to carry out low-moisture fermentations. Fluidizable granulated microorganisms are used for this fermentation under sterile conditions in the fluidized bed fermenter which is initially operated as a bubble column.

5 Claims, 1 Drawing Sheet

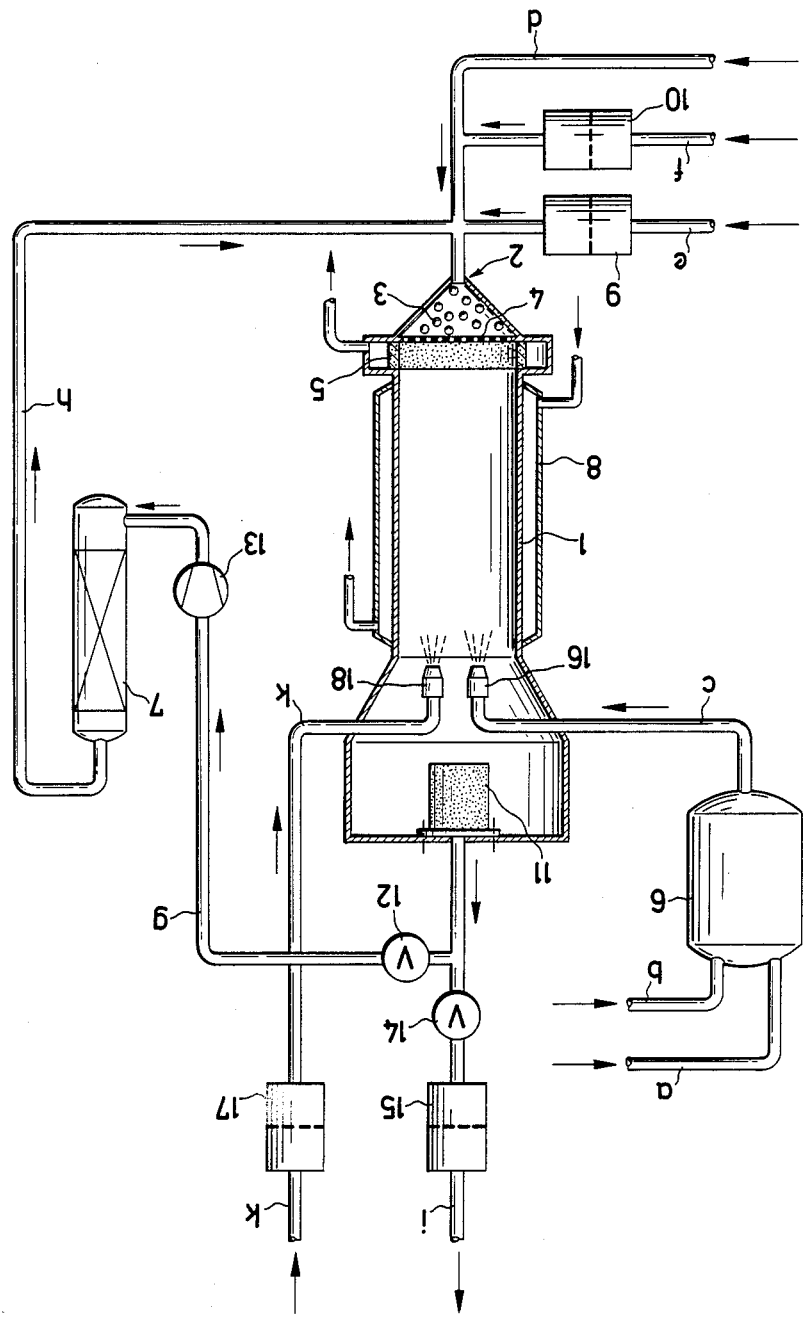

STERILIZABLE FLUIDIZED BED FERMENTER

DESCRIPTION

The invention relates to a sterilizable fluidized bed fermenter for carrying out low-moisture fermentations, in which use is made of microorganisms which are cultured under sterile conditions in the fluidized bed fermenter itself, which is initially operated as a bubble column, and are converted into fluidizable granules.

Fluidized bed fermenters have a wide variety of uses in biotechnological processes. Thus, there is a description in European Patent Application No. 58 426 of a process for the preparation of ethanol by fermentation of carbohydrates, in which microorganisms suitable for ethanol production are placed in the form of free-flowing particles in a bed which is fluidized with gas, and aqueous nutrient solutions containing one or more fermentable carbohydrates are passed into the bed of fluidized particles and fermented therein. The conditions of this fermentation are essentially set up by the temperature and the partial pressure of oxygen in the gas which is flowing as a continuous phase into the fluidized bed. A process of this type allows ethanol to be produced without pot ale. This process is carried out in a fermenter which is initially charged with the free-flowing microorganism particles and into which is fed from a reservoir an aqueous carbohydrate-containing nutrient solution via a spray nozzle which is mounted over the fluidized bed. The resulting water/alcohol mixture is condensed in a condenser, and the fermenter is supplied with fresh gas at a constant temperature.

The wide variety of possible uses of reactions in fluidized bed fermenters is evident from European Patent Application No. 106 146 in which a large number of different microbial metabolites and enzymes are produced by biological routes by fermentative conversion of precursors or by addition of effectors. This entails the microorganisms being converted into fluidizable granules. The precursors or effectors are either incorporated in the granules beforehand or sprayed as solution or suspension onto the granules in the fluidized bed fermenter. It is possible with a process of this type to produce acceptable yields of substances which are accessible by methods of chemical synthesis only with difficulty or not at all.

Moreover, there is a description in U.S. Pat. No. 4,046,921 of a process in a fluidized bed fermenter, in which microorganisms immobilized on solid carriers are fluidized by an upward-directed stream of gas and sprayed with a nutrient solution. This patent also expressly mentions the problem that it is possible for the microorganism to be contaminated by undesired foreign microbes. To prevent the hazards associated with this, substances having fungicidal or bactericidal activity are added to the nutrient solution in order to prevent growth of microorganisms from the families of Pseudomonadaceae, Achromobacteriaceae, Enterobacteriaceae, Micrococci or Lactobacillaceae. In addition, it is recommended that sulfur dioxide be added to the gas passed into the fluidized bed fermenter for cooling, in order thus to eliminate undesired microbes. However, this treatment also has adverse effects on the microorganisms necessary for the process which is to be carried out.

Since the exclusion of foreign microbes is crucial for the yield of microbial processes and the purity of the resulting products, the object was to develop a fluidized bed fermenter which is sterilizable and permits fermentations to be carried out under sterile conditions.

Hence, the invention relates to a sterilizable fluidized bed fermenter for carrying out low-moisture fermentations, in which use is made of microorganisms which are cultured under sterile conditions in the fluidized bed fermenter itself, which is initially operated as a bubble column, and are converted into fluidizable granules, which has the following features.

(a) the fluidized bed fermenter (1) has at the bottom an orifice (2) for introducing a stream of gas, and an inlet bottom section (3) with a perforated or sintered disk (4) for distributing the stream of gas, (b) one or more filter elements (5) are mounted on the side of the bottom part of the fluidized bed fermenter and can be used to draw off the used culture broth under sterile conditions, (c) there is provision of a reservoir (6) which is provided with a steam line (a) and a substrate line (b), from which the fluidizable granules can be sprayed with nutrient solution through a line (c) and a nozzle (16), (d) there is a temperature-controllable air humidifier (7) which prevents the microorganisms being dried out by the stream of gas, and (e) there is a device for introducing superheated steam (lines (a) and (d)), a jacket heat-exchanger or a heating element (8) for sterilizing all the fittings of the fluidized bed fermenter which are in direct contact with the microorganisms.

Prevention of entry of foreign microbes into the fermentation mixture is initially effected by the fluidized bed fermenter (1) according to the invention in that, on the one hand, the fermenter is sterilized before the start of the fermentation by introducing superheated steam through lines (a) and (d) or by heating the fermenter by a jacket heat-exchanger or a heating element (8). Once the fluidized bed fermenter has been prepared in this way the procedure is not, for example, to introduce the biomass of the microorganism which has already been cultured in another fermenter, which would certainly result in contamination with foreign microbes, on the contrary the fluidized bed fermenter is charged, under the sterile conditions normally used, only with an inoculum cultured in a small fermenter, and a submerged culture of the microorganism is carried out in the fluidized bed fermenter itself, which is initially operated as bubble column. During this it is possible to add nutrient-containing carriers such as rice grains, coarse soymeal or rolled oats, on which the microorganisms grow. This promotes the formation of aggregates and colonies of microorganisms. Of course, there are also microorganisms which form aggregates or colonies without solid carriers of this type.

As soon as an adequate quantity of microorganisms has been produced, the used substrate solution is removed through filter elements (5) which are installed near the base of the fermenter. Suitable filter elements are sintered filters, membrane filters or Fuji blades which, if necessary, can likewise be sterilized with superheated steam. The pore size of the filter elements should be selected so that cell agglomerates and cell colonies are retained but solvent and single cells can pass through. This procedure ensures that the fluidized bed fermenter now contains a culture of one microorganism which is not contaminated by foreign microbes.

For carrying out the actual fluidized bed reaction, the mass of microorganisms from which used culture broth has been removed until a pasty consistency has been reached is fluidized from below by introducing a stream of gas through the orifice (2). For this purpose, compressed air (e) or oxygen (f) is used, having previously been forced through the bacterial filters (9) or (10) so that no foreign microorganisms can be carried by the stream of gas into the fluidized bed reactor.

The gas used for fluidizing the biological material leaves the fluidized bed reactor via the membrane filter candle (11) and can then be recirculated through the valve (12). The stream of gas is then passed through the line (g) via the circulating gas blower (13) into the temperature-controllable air humidifier (7), and then the cooled and moisture-saturated gas is once more introduced into the fermenter through the line (h) and via the orifice (2). Alternatively, it is also possible for the stream of gas to be passed straight through, in which case it then leaves the fermenter via the membrane filter candle (11), valve (14) and the filter element (15) and via the outflow line (i).

The nutrient solution which is required for growth during the fluidized bed fermentation is located in the reservoir (6) and is sprayed via the line (c) and the nozzle (16) in the form of finely divided droplets into the reactor, unless the microorganisms utilize the nutrient-containing carrier on which they have grown as the exclusive source of nutrients.

Special precautions must be taken to prevent the microorganisms drying out. The temperature-controllable air humidifier (7), which ensures that the introduced stream of gas is saturated with moisture, is not the only way of accomplishing this. In addition, if necessary it is possible to introduce into the fermenter, at any time, microbe free water through the line (k) via the filter element (17) and the nozzle (18), and thus moisten the microorganisms.

During the fermentation there is a continuous increase in the $CO_2$ content of the circulating gas, and a corresponding decrease in the oxygen content. However, a constant composition of the gas is a prerequisite for optimal fermentation. For this reason the fluidized bed fermenter according to the invention is equipped with control elements (which are not shown in the drawing) which control the continuous removal of the carbon dioxide via the membrane filter candle (11) and the filter element (15). The amounts of gas removed are replaced by supplying oxygen or air through the bottom orifice (2).

It is necessary in fluidized bed reactions to take particular care that the evolved heat of reaction is removed.

For this reason, the stream of gas entering through the bottom orifice (2) is cooled as it passes through the temperature-controllable air humidifier (7). In addition, the fluidized bed fermenter (1) is provided with an outer cooling jacket. If the cooling of the biological material achieved with this is still inadequate, the excess heat is removed by evaporative cooling. The amount of water which is lost by this is replenished by addition of microbe-free water through the nozzle (18).

The examples which follow show possible uses of the fluidized bed fermenter according to the invention:

EXAMPLE 1

A culture of the strain *Streptomyces griseus* DSM 40693 was cultivated in a small fermenter of capacity 15 l to give a well grown inoculum in 3 days. The medium contained 60 g of casein peptone, 60 g of meat extract, 7.5 g of yeast extract and 37.5 g of sodium chloride. Incubation was carried out at 35° C. with 7.5 l air/min and a stirrer speed of 500 rpm at pH 7.2. This culture was used to inoculate the fluidized bed fermenter according to the invention which had previously been sterilized at 121° C. for 30 min in the presence of a nutrient medium which contained 3.4 kg of casein peptone, 1.2 kg of meat extract, 150 g of yeast extract and 750 g of sodium chloride in 250 l of water. A solution of 3 kg of glucose, 3 kg of maltodextrin from cornstarch and 35 l of water which had been prepared separately and sterilized was added to the total mixture before inoculation.

The fluidized bed fermenter was then inoculated and operated as a bubble column aerating at 300 l/min, during which the temperature was maintained at 35° C. and the pH at between 6.8 and 7.5.

The *Streptomyces griseus* biomass reach a dry weight of 3.72 kg within 48 hours. Thereafter liquid was sucked out through the filter elements (4) until 30 l still remained in the culture vessel. This liquid formed together with the accumulated *Streptomyces griseus* cells a pasty mass which was fluidized by appropriately increasing the air input. Over a period of a further 48 hours, 1 l of a sterile solution composed of 5% casein peptone, 4% glucose and 4% maltodextrin was sprayed each hour into the fluidized culture mass. The *Streptomyces griseus* biomass grew to a dry weight of 5.63 kg in these 48 hours.

EXAMPLE 2

A culture of the strain *Streptomyces griseus* DSM 40693 was precultivated in a small fermenter as in Example 1 and used as inoculum for the fluidized bed fermenter according to the invention. A nutrient medium composed of 6 kg soymeal and 1.5 kg comminuted rolled oats in 250 l water had previously been made up, and sterilized at 121° C. for 45 min, in the latter. The nutrient medium was cooled to a temperature of 30° C. and maintained at this for 40 hours, and then sterilized once more at 121° C. for 45 min. Then a solution of 1.5 kg of glucose and 3 kg of maltodextrin from cornstarch in 35 l of water which had been prepared separately and sterilized was added, and the mixture was inoculated. The culture conditions were the same as in Example 1.

In the period of 48 hours the culture grew to a satisfactory density of mycelium. During this the sediment (PMV) rose from 6% to 15%. Liquid was removed from the culture as in Example 1 until a pasty residue of 60 l was left.

This mass was incubated further as a fluidized bed. The dry weight of the biomass (determined by centrifugation of an aliquot at 4000 rpm for 10 minutes) was 17.8 kg, and this increased to 26.4 kg in the subsequent 48 hours (including the undissolved constituents of the nutrient medium). The nutrient medium and the treatment of the biomass in this period were the same as in Example 1.

EXAMPLE 3

A culture of the fungal strain *Penicillium roqueforti* DSM 1079 was cultivated as a preculture in a small fermenter of capacity 15 l. The nutrient medium contained 300 g of malt extract, 30 g of yeast extract, 150 g of glucose and 7.5 g of $(NH_4)_2HPO_4$. Culturing lasted 4 days at 23° C. with aeration at 7.5 l/min and a stirrer speed of 300 rpm. The pH was maintained between 6.4 and 6.8. Before transferring this culture into the fluidized bed fermenter according to the invention, in the latter a nutrient medium composed of 12 kg of malt extract, 900 g of yeast extract and 600 g of $(NH_4)_2HPO_4$ in 230 l of water was sterilized at 121° C. for 30 min. 6 kg of glucose were separately dissolved in 35 l of water, sterilized and added to the total mixture. After the fluidized bed fermenter had been inoculated it was operated for 72 hours as a bubble column at 23° C. with aeration at 180 l air/min. The pH was maintained between 6.4 and 6.8. After the first 24 hours had elapsed, a concentrate composed of 6 kg of glucose and 3 kg of malt extract in 20 l of water was steadily metered into the culture. The fungal biomass grew in the 72 hours to 17.3 kg dry matter. The liquid was then sucked out as in Example 1, and a pasty residue of 60 l was left in the reactor. The latter was incubated as a fluidized bed for 96 hours. During this period a solution composed of 6% malt extract, 6% glucose and 0.3% $(NH_4)_2HPO_4$ was sprayed into the reactor in an amount of 1 l/hour. During this, the fungal mycelium grew further to 24.5 kg dry matter.

EXAMPLE 4

A preculture of the strain *Penicillium roqueforti* DSM 1079 was prepared as described in Example 3 and used for inoculation of the previously sterilized fluidized bed fermenter. The nutrient medium, which was prepared in the fluidized bed fermenter, contained 6 kg of malt extract, 600 g of yeast extract and 150 g of $(NH_4)_2HPO_4$ in 250 l of water. Separately, a solution of 3 kg of glucose in 35 l of $H_2O$ was prepared and sterilized. The culture was then operated as a bubble column for 36 hours. During this period, the fungal mycelium grew to 4.6 kg dry matter. Thereafter, the liquid was sucked out until a residue of 25 l was left. The pasty mass was incubated further as a fluidized bed for 96 hours. In the first half of this period 40 kg of curd cheese were metered in. The fungus adhered to the curd cheese to form coarse particles which, at the end of the incubation time, were completely permeated and had the aroma typical of the fungus used.

EXAMPLE 5

A culture of the yeast *Schizosaccharomyces pombe* DSM 70577 was cultivated as a preculture in the nutrient medium described in Example 3 in a small fermenter of capacity 15 l. Culturing lasted 30 hours at 35° C., during which 7.5 l air/min were introduced and a stirrer speed of 500 rpm was used. The pH was maintained at 5.6 to 6.0. This culture was then transferred into the previously sterilized fluidized bed fermenter according to the invention. The fluidized bed fermenter contained a nutrient medium composed of 21 kg of malt extract, 3 kg of meat extract and 1.5 kg of casein peptone in 285 l of water, which had been sterilized at 121° C. for 30 min. This culture was then operated as a bubble column at 35° C. for 48 hours, 180 l air/min being introduced, and the pH being maintained between 5.6 and 6.0. During this period, a hot sterilized solution composed of 3 kg of glucose in 10 l of water was continuously added. The yeast mass grew in this period to a dry weight of 5.8 kg. Subsequently the used culture broth was sucked out through sterile filters until a residue of 30 l was left. The paste, which was still mobile, was incubated further as a fluidized bed. The air throughput was increased until satisfactory fluidizing took place. During a further 48 hours, 1 l/hour of a sterile solution of 20% malt extract, 6% glucose and 3% casein peptone was sprayed into the reactor. The yeast biomass grew further in this time to a dry weight of 11.8 kg.

We claim:

1. A sterilizable fluidized bed fermenter for carrying out low-moisture fermentations, in which use is made of microorganisms which are cultured under sterile conditions in the fluidized bed fermenter itself, which is initially operated as a bubble column, and are converted into fluidizable granules, which has the following features
    (a) the fluidized bed fermenter (1) has at the bottom an orifice (2) for introducing a stream of gas, and an inlet bottom section (3) with a perforated or sintered disk (4) for distributing the stream of gas,
    (b) one or more filter elements (5) are mounted on the side of the bottom part of the fluidized bed fermenter and can be used to draw off the used culture broth under sterile conditions,
    (c) there is provision of a reservoir (6) which is provided with a steam line (a) and a substrate line (b), from which the fluidizable granules can be sprayed with nutrient solution through a line (c) and a nozzle (16),
    (d) there is a temperature-controllable air humidifier (7) which prevents the microorganisms being dried out by the stream of gas, and
    (e) there is a device for introducing superheated steam, a jacket heat-exchanger or a heating element (8) for sterilizing all the fittings of the fluidized bed fermenter which are in direct contact with the microorganisms.

2. A fluidized bed fermenter as claimed in claim 1, wherein the stream of gas introduced through the bottom orifice (2) to fluidize the microorganisms is recirculated.

3. A fluidized bed fermenter as claimed in claim 1, wherein the stream of gas introduced through the bottom orifice (2) to fluidize the microorganisms is passed straight through.

4. A fluidized bed fermenter as claimed in claim 1, wherein the gases formed in the fermentation are removed through a membrane filter candle (11), a valve (14) and an additional filter element (15).

5. A fluidized bed fermenter as claimed in claim 3, wherein the amounts of gas formed during fermention which are removed from the fermeter are replaced by introducing oxygen or air through the bottom orifice (2).

* * * * *